United States Patent
Brambilla et al.

(10) Patent No.: US 9,782,553 B2
(45) Date of Patent: Oct. 10, 2017

(54) PATIENT INTERFACE AND NON-INVASIVE POSITIVE PRESSURE VENTILATING METHOD

(75) Inventors: Enrico Brambilla, Drummoyne (AU);
Renee Frances Doherty, Coogee (AU);
Philip Rodney Kwok, Chatswood (AU)

(73) Assignee: ResMed Limited, Bella Vista (AU)

( * ) Notice: Subject to any disclaimer, the term of this patent is extended or adjusted under 35 U.S.C. 154(b) by 2358 days.

(21) Appl. No.: 12/134,801

(22) Filed: Jun. 6, 2008

(65) Prior Publication Data
US 2009/0014007 A1    Jan. 15, 2009

Related U.S. Application Data

(60) Provisional application No. 60/949,692, filed on Jul. 13, 2007.

(51) Int. Cl.
*A61M 16/00* (2006.01)
*A61M 16/06* (2006.01)

(52) U.S. Cl.
CPC ........ *A61M 16/06* (2013.01); *A61M 16/0616* (2014.02); *A61M 2205/42* (2013.01)

(58) Field of Classification Search
CPC .......... A61M 16/0605; A61M 16/0622; A61M 16/06; A61M 16/0616; A61M 2205/42
(Continued)

(56) References Cited

U.S. PATENT DOCUMENTS 4,770,169 A * 9/1988 Schmoegner et al. ... 128/207.13
5,647,357 A * 7/1997 Barnett et al. ........... 128/206.24
(Continued)

FOREIGN PATENT DOCUMENTS

WO    WO 2006/102707 A1    10/2006
WO    WO 2006/113321 A2    10/2006

OTHER PUBLICATIONS

Hans Rudolph, Inc., "Ultimate Seal User Application Instructions," May 1998, 1 page.
(Continued)

*Primary Examiner* — Bradley Philips
(74) *Attorney, Agent, or Firm* — Nixon & Vanderhye P.C.

(57) ABSTRACT

A patient interface for use in delivering a flow of breathable gas to an airway of a patient includes a first seal adapted to contact the patient's face and seal a first space between the patient interface and the patient's face at a first positive pressure; and a second seal adapted to contact the patient's face and seal a second space between the patient interface and the patient's face at a second positive pressure. The first seal also seals the first space from the second space. A leak reducing element may be provided on a seal to reduce and/or diffuse leakage of gas. A vacuum line configured to create a negative pressure may be provided in the second space to remove any gas leaking from the first space to the second space. A seal may be connected to a conduit for delivering the flow of gas that is incorporated into a frame of the patient interface. The seal may be inflatable by the flow of breathable gas to pressurize the seal against the patient's face and include a vent that directs the flow of breathable gas to a space between the patient interface and the patient's face. A cuff may be provided over the seal in the nasal bridge region to direct any leakage of the gas flow from the seal in the nasal bridge region in a direction away from the patient's eyes.

42 Claims, 8 Drawing Sheets

(58) Field of Classification Search
USPC .................................................. 128/206.24
See application file for complete search history.

(56) References Cited

U.S. PATENT DOCUMENTS

| | | | | |
|---|---|---|---|---|
| 5,662,101 | A * | 9/1997 | Ogden et al. ............ | 128/205.25 |
| 6,035,852 | A * | 3/2000 | Hoftman .................. | 128/206.26 |
| 6,082,360 | A * | 7/2000 | Rudolph et al. ......... | 128/206.25 |
| 6,357,440 | B1 * | 3/2002 | Hansen et al. ........... | 128/206.19 |
| 6,418,928 | B1 * | 7/2002 | Bordewick et al. ..... | 128/205.25 |
| 6,651,661 | B2 * | 11/2003 | Matioc ..................... | 128/205.25 |
| 6,748,949 | B2 * | 6/2004 | Smaldone ................ | 128/203.29 |
| 6,834,650 | B1 | 12/2004 | Fini et al. | |
| 7,044,130 | B2 * | 5/2006 | Jones et al. .............. | 128/206.21 |
| 7,287,528 | B2 | 10/2007 | Ho et al. | |
| 7,640,933 | B1 * | 1/2010 | Ho ........................... | 128/206.24 |
| 7,743,768 | B2 * | 6/2010 | Ho et al. .................. | 128/206.24 |
| 2003/0029455 | A1 | 2/2003 | Smith et al. | |
| 2003/0168063 | A1 * | 9/2003 | Gambone ............. | A61M 16/06 128/203.16 |
| 2008/0053451 | A1 * | 3/2008 | Bordewick et al. ..... | 128/207.11 |
| 2011/0088699 | A1 * | 4/2011 | Skipper et al. .......... | 128/206.26 |

OTHER PUBLICATIONS

Hans Rudolph, Inc., "Nasal CPAP Mask & Mask Seals (Comfort Seal & Ultimate Seal)," downloaded from www.medcatalog.com, with enlarged image of "A New Nasal CPAP/Bilevel Mask," dated Sep. 2000 (3 pages).

* cited by examiner

PATIENT INTERFACE AND NON-INVASIVE POSITIVE PRESSURE VENTILATING METHOD

CROSS REFERENCE TO RELATED APPLICATION

This application claims priority to U.S. Provisional Application 60/949,692, filed Jul. 13, 2007, the entire contents being incorporated herein by reference.

FIELD OF THE INVENTION

Sample embodiments of the present invention relate to a patient interface for use in delivering a flow of breathable gas to an airway of a patient. Sample embodiments of the present invention also relate to a non-invasive positive pressure ventilating method.

BACKGROUND OF THE INVENTION

Non-invasive positive pressure ventilation (NIPPV) techniques, such as, for example, the application of continuous positive airway pressure (CPAP) have been used to treat sleep disorder breathing (SDB) such as obstructive sleep apnea (OSA) and other disorders such as chronic obstructive pulmonary disease (COPD) and congestive heart failure (CHF). Apparatuses for applying NIPPV techniques typically include a flow generator, including a blower, and a patient interface. A delivery conduit or hose is connected between the flow generator and the patient interface to deliver breathable gas at a positive pressure to the patient. A number of different patient interfaces are known and include, for example, nasal masks, nose and mouth masks, full-face masks, and nasal prongs and pillows. A headgear is typically utilized to position the patient interface on the patient's face and counterbalance the force of gravity and the force which results from the application of pressurized air which seeks to push the mask off the face.

NIPPV therapies are typically administered at night while the patient sleeps. In order for the therapy to be effective, the patient interface must be comfortable enough for the patient to remain sleeping, while maintaining a seal that is sufficient to deliver the breathable air at the required pressure.

Air leakage from between the patient's skin and the patient interface reduces the effectiveness of the therapy. Even very small leaks can be perceived by the patient and/or bed partner. The air leakage may cause the patient to increase the pressure of the mask against the patient's face. The air leakage may also cause the flow generator to increase the pressure of the delivered air, thus increasing the speed and noise of the flow generator. Increasing the pressure of the delivered air results in an increase in the flow of air, including the vent flow and leak flow. If a humidifier is used, the increase in the leak flow results in a waste of water from the humidifier. If supplemental oxygen is being provided to the flow of air, the increase in the leak flow causes a waste of some of the supplemental oxygen. Moreover, the air leakage may act as an irritant to the patient's eyes and disturb the patient's sleep.

Various masks have been proposed for minimizing leakage between the mask cushion and the face of the patient. Examples of these respiratory masks are disclosed in U.S. Patent Application Publication 2003/0029455, U.S. Pat. No. 6,418,928 and WO Patent Application Publication 2006/113321. Other approaches to minimizing leakage include attempting to provide a perfect seal between the patient's face and the patient interface. U.S. Pat. No. 6,834,650 is an example of such an attempt. WO Patent Application Publication 2006/102707 discloses a patient interface having a vacuum line as a return path from the patient interface. Leakage is prevented, but requires the use of non-vented patient interfaces.

There still exists a need for a patient interface that controls leakage and improves therapy for the patient by reducing, or eliminating, the main discomfiture associated with leakage.

SUMMARY OF THE INVENTION

One aspect of the invention relates to a patient interface that improves therapy to a patient by reducing, or eliminating, problems caused by leakage from the patient interface.

Another aspect of the invention relates to a patient interface that improves therapy to a patient by reducing, or eliminating, patient discomfort caused by leakage from the patient interface.

Yet another aspect of the invention relates to a patient interface that reduces, or eliminates, the occurrence of explosive, or bursting, leakage.

Still another aspect of the invention relates to a patient interface that can catch or collect leakage from a first seal with a second seal to prevent leakage from the patient interface.

An even further aspect of the invention relates to a patient interface that increases the resistance to leakage.

A still further aspect of the invention relates to a patient interface that diffuses leakage to reduce irritation to the patient.

Another aspect of the invention relates to a patient interface that vents or deflects leakage to reduce or prevent disturbance to the patient.

According to one embodiment of the invention a patient interface for use in delivering a flow of breathable gas to an airway of a patient is provided. The patient interface comprises a first seal adapted to contact the patient's face and seal a first space between the patient interface and the patient's face at a first positive pressure; and a second seal adapted to contact the patient's face and seal a second space between the patient interface and the patient's face at a second positive pressure. The first seal is configured to seal the first space from the second space.

According to another embodiment of the invention, a patient interface for use in delivering a flow of breathable gas to an airway of a patient comprises a seal adapted to contact the patient's face and seal a space between the patient interface and the patient's face at a positive pressure; and a leak reducing means provided on the seal for reducing leakage of gas from the space.

According to a further embodiment of the invention, a patient interface for use in delivering a flow of breathable gas to an airway of a patient comprises a first seal adapted to contact the patient's face and seal a first space between the patient interface and the patient's face at a first positive pressure; and a second seal adapted to contact the patient's face and seal a second space between the patient interface and the patient's face. A vacuum line is configured to create a negative pressure in the second space and remove any gas leaking from the first space to the second space. The negative pressure is sufficient to deform the first and second seals and a portion of the patient's face covered by the second space.

According to yet another embodiment of the invention, a patient interface for use in delivering a flow of breathable gas to an airway of a patient comprises a frame; and a conduit for delivering the flow of breathable gas. The conduit is incorporated with the frame. A seal is connected to the conduit. The seal is inflatable by the flow of breathable gas to pressurize the seal against the patient's face and includes a vent to direct the flow of breathable gas to a space between the patient interface and the patient's face.

According to still another embodiment of the invention, a patient interface for use in delivering a flow of breathable gas to an airway of a patient comprises a seal adapted to contact the patient's face and seal a space between the patient interface and the patient's face. The sealed space includes a nasal bridge region of the patient's face. A cuff is provided over the seal in the nasal bridge region to direct any leakage of the gas flow from the seal in the nasal bridge region in a direction away from the patient's eyes.

According to another embodiment of the invention, a non-invasive positive pressure ventilating method comprises delivering a flow of breathable gas to a patient interface; sealing a first space between the patient interface and the patient's face at a first positive pressure; and sealing a second space between the patient interface and the patient's face at a second positive pressure. The first space is sealed from the second space.

According to still another embodiment of the invention, a non-invasive positive pressure ventilating method comprises delivering a flow of breathable gas to a patient interface; sealing a first space between the patient interface and the patient's face at a first positive pressure; and diffusing any leakage from the sealed first space.

According to a further embodiment, a non-invasive positive pressure ventilating method comprises delivering a flow of breathable gas to a patient interface; sealing a first space between the patient interface and the patient's face at a first positive pressure; and deflecting any leakage of air from the first space in a nasal bridge region away from the patient's eyes.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings:

FIGS. 3b, 3c, 3d, and 3e illustrate different foam shapes that may be used with the patient interference of FIG. 3a;

DETAILED DESCRIPTION OF THE ILLUSTRATED EMBODIMENTS

The following description is provided in relation to several embodiments which may share common characteristics and features. It is to be understood that one or more features of any one embodiment may be combinable with one or more features of the other embodiments. In addition, any single feature or combination of features in any of the embodiments may constitute additional embodiments.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

The term "air" will be taken to include breathable gases, for example air with supplemental oxygen. It is also acknowledged that the blowers described herein may be designed to pump fluids and/or gases other than air.

Patient Interface Models

Figure 1:
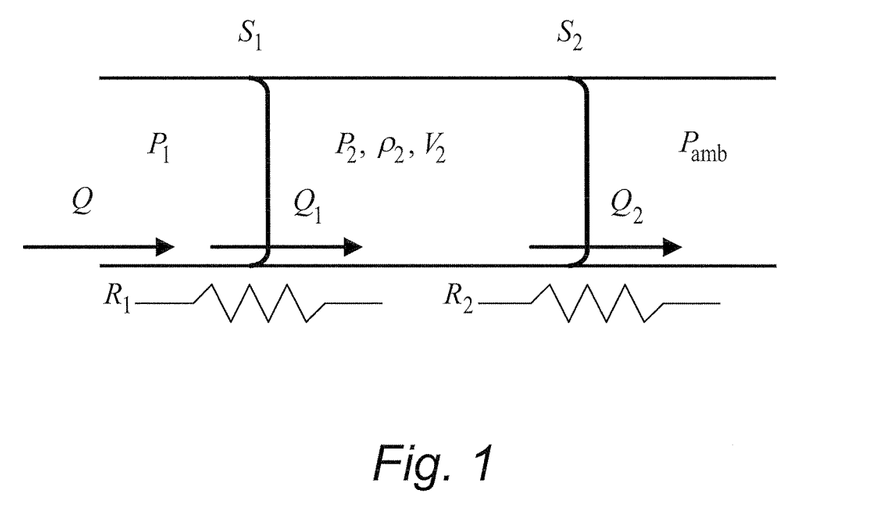
FIG. 1 is a model according to an example of the present invention that illustrates leakage from a patient interface having two seals in series.

Referring to FIG. 1, a patient interface may include two seals $S_1$, $S_2$ that are provided in series. Each seal $S_1$, $S_2$ has a resistance $R_1$, $R_2$, respectively, to leakage. A pressure $P_1$ is delivered at the patient interface by a flow generator. A pressure $P_2$ exists between the two seals $S_1$, $S_2$. Ambient pressure $P_{amb}$ is provided outside the patient interface.

When the pressure $P_1$ delivered at the patient interface by the flow generator is greater than the maximum pressure $P_{1max}$ that the first seal can withstand, then the seal $S_1$ breaks and a leak flow Q occurs against the resistance $R_1$. Initially, a leak flow $Q_1$ flows across the first seal $S_1$. In the space between the first seal $S_1$ and the second seal $S_2$, a pressure $P_2$ develops as a result of the leak flow $Q_1$. The pressure $P_2$ is a positive pressure, i.e., greater than ambient pressure $P_{amb}$. If the pressure $P_2$ is greater than the maximum pressure $P_{2max}$ that the seal $S_2$ can withstand, a second leak flow $Q_2$ flows across the second seal $S_2$ and out of the patient interface into the ambient air.

The space between the first and second seals $S_1$, $S_2$ has a volume $V_2$ that contains a volumetric mass $\rho_2$ of breathable gas (e.g. air).

Various conditions may be present at the patient interface. In designing a seal arrangement for a patient interface, the various conditions may be considered in addition to the desired status of the patient interface. For example, the seal arrangement of the patient interface may be designed to collect and/or control any possible leakage, including any leakage between the first and second seals, and/or any leakage from the second seal, i.e., leakage out of the patient interface. As another example, seal arrangement may be designed to avoid leakage by sealing properly under any condition. The seal arrangement should thus be designed to avoid leakage that causes annoyance and/or discomfort to the patient, and to improve the quality of the therapy by reducing, or eliminating, problems associated with leakage, e.g., disruption of bi-level algorithms for control of the flow generator.

Although a seal arrangement that prevents all leakage, i.e., a perfect seal, would be the most desired arrangement, such an arrangement is very difficult to achieve. Such a seal arrangement may have a desired effect in a relatively small number of cases, for example in high pressure bi-level devices. A more practical seal arrangement may be provided to control leakage when it occurs. Such an arrangement would have a desired effect in a larger number of cases. Controlling leakage allows the flow generator to react properly to leakage, and thus improves the delivery of the therapy. Controlling leakage may also prevent the leakage from causing patient discomfort. Preventing disturbance of the patient's sleep is one way to ensure proper treatment.

A seal arrangement for a patient interface according to the invention may be designed to prevent explosive leak from the patient interface. The seal arrangement according to examples of the invention may also be designed to reduce or eliminate noise disturbance to the patient, and to reduce or eliminate eye irritation by reducing or eliminating leakage. Other design objectives than those specifically discussed herein may also be considered.

Figure 2:
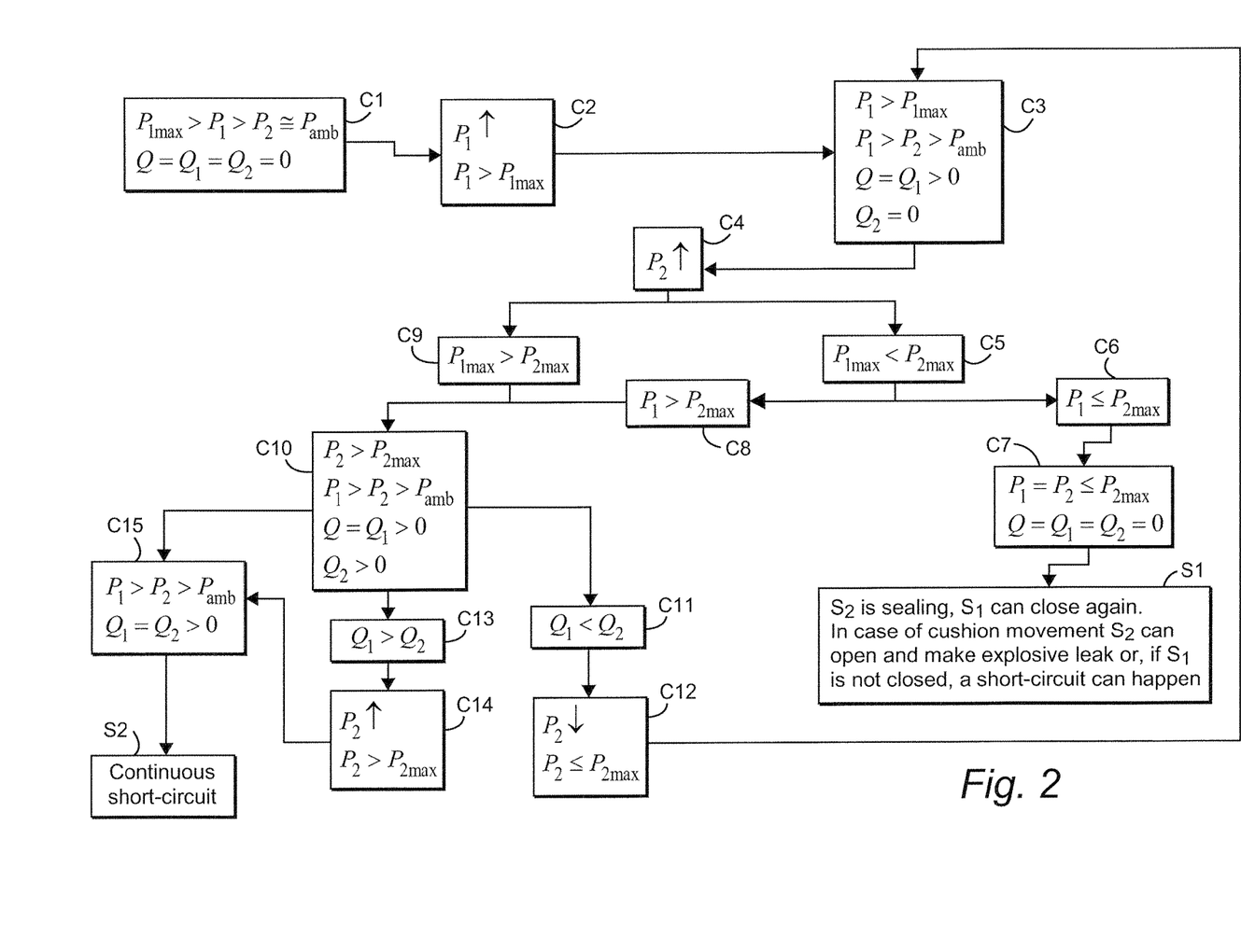
FIG. 2 is a model according to an example of the present invention that illustrates different possible conditions and resulting statuses that may evolve for a patient interface having two seals provided in series.

Referring to FIG. 2, a model which may be used in designing patient interfaces according to examples of the invention is illustrated. As shown in condition C1, when the maximum sealing pressure $P_{1max}$ of the first seal $S_1$ is larger than the pressure $P_1$ delivered at the mask by the flow generator, and greater than the pressure $P_2$ between the first and second seals $S_1$, $S_2$, there is no leak flow across the first and second seals $S_1$, $S_2$, i.e., $Q=Q_1=Q_2=0$.

If the condition C1 is changed by another condition C2 that increases the pressure $P_1$ delivered at the patient interface by the flow generator so that the pressure $P_1$ exceeds the maximum sealing pressure $P_{1max}$ of the first seal $P_1$, another set of conditions C3 occurs at the patient interface. Under the conditions C3, the pressure $P_1$ delivered by the flow generator exceeds the maximum sealing pressure $P_{1max}$ of the first seal $S_1$, and also exceeds the pressure $P_2$ between the first and second seals $S_1$, $S_2$ and the ambient pressure $P_{amb}$. Under these conditions C3, a leak flow $Q_1$ occurs across the first seal $S_1$. However, there is no leak flow across the second seal $S_2$, i.e., $Q_2=0$. Accordingly, there is no leakage from the patient interface to the ambient.

The leak flow $Q_1$ across the first seal $S_1$ may cause the pressure $P_2$ between the first seal $S_1$ and the second seal $S_2$ to increase (condition C4). As the pressure $P_2$ between the first and second seals $S_1$, $S_2$ increases, additional design conditions C5, C9 may effect the performance of the patient interface. Under a first design condition C5, the maximum sealing pressure $P_{1max}$ of the first seal $S_1$ is less than the maximum sealing pressure $P_{2max}$ of the second seal $S_2$. Under this design condition C5, if the pressure $P_1$ delivered by the flow generator at the patient interface is less than or equal to the maximum sealing pressure $P_{2max}$ of the second seal $S_2$ (condition C6), then the pressure $P_2$ between the first and second seals $S_1$, $S_2$ equals the pressure $P_1$ delivered by the flow generator (condition C7) As delivered pressure $P_1$ is less than the maximum sealing pressure $P_{2max}$ of the second seal $S_2$, the leak flow Q, including the leak flow $Q_1$ across the first seal and the leak flow $Q_2$ across the second seal $S_2=0$.

When the conditions C1-C7 discussed above are satisfied, the patient interface assumes a first status S1. In this status S1, the second seal $S_2$ is in sealing engagement with the patient's face to prevent leakage. The first seal $S_1$ does not seal against the patient's face, but may return to a sealing engagement upon a change of condition(s). When the patient interface is in the first status S1, and the cushion is moved, such as during the patient's sleep session, the second seal $S_2$ may open and allow an explosive leak of air from the patient interface. If the first seal $S_1$ is not in sealing condition, a short circuit may occur when the cushion moves so that a leak flow occurs across both the first and second seals $S_1$ and $S_2$.

Referring back to the condition C5 ($P_{1max}<P_{2max}$), if the pressure $P_1$ at the patient interface delivered by the flow generator exceeds the maximum sealing pressure $P_{2max}$ of the second seal (condition C8), another condition C10 develops. It is also possible for the condition C10 to develop when the pressure $P_2$ between the first and second seals is increasing (condition C4) and the maximum sealing pressure $P_{1max}$ of the first seal $S_1$ is greater than the maximum sealing pressure $P_{2max}$ of the second seal $S_2$ (condition C9).

In condition C10, the pressure $P_2$ between the first and second seals exceeds the maximum sealing pressure $P_{2max}$ of the second seal $S_2$. The pressure $P_1$ delivered by the flow generator also is greater than the pressure $P_2$ between the seals, which is greater than the ambient pressure $P_{amb}$. Under this condition C10, a leak flow Q includes a leak flow $Q_1$ across the first seal $S_1$ and a leak flow $Q_2$ across the second seal $S_2$.

If the flow $Q_1$ across the first seal $S_1$ is less than the flow $Q_2$ across the second seal $S_2$ (C11) and the pressure $P_2$ between the first and second seals is decreasing such that the pressure $P_2$ is less than or equal to the maximum sealing pressure $P_{2max}$ of the second seal $S_2$ (C12), the patient interface returns to condition C3. In condition C3, there is a flow $Q_1$ across the first seal $S_1$, but no flow across the second seal $S_2$ (i.e. $Q_2=0$). This can cause cyclic explosive leaks.

If the leak flow $Q_1$ across the first seal $S_1$ is greater than the leak flow $Q_2$ across the second seal $S_2$ (condition C13) and the pressure $P_2$ between the first and second seals is increasing such that the pressure $P_2$ is greater than the maximum sealing pressure $P_{2max}$ of the second seal $S_2$ (condition C14), the leak flows $Q_1$, $Q_2$ across the first and second seals $S_1$, $S_2$ will equalize to a value greater than 0 (condition C15) This condition C15 may also result directly from condition C10 if the leak flows Q1, Q2 across the first and second seals S1, S2 are both greater than zero and equal to each other.

In condition C15, the pressure $P_1$ at the patient interface delivered by the flow generator is greater than the pressure $P_2$ between the first and second seals, which is greater than ambient pressure. If this condition C15 is present, the patient interface is in a second status S2 in which there is a continuous leak, or short circuit, through both the first and second seals. As discussed below, various seal arrangements may be designed to reduce or eliminate the problems associated with a continuous leak as occurs in the second status S2.

The model discussed above with respect to FIG. 2 may rely on certain assumptions. For example, it may be assumed that there are no relative movements between the patient's face and the patient interface. It may also be assumed that a leak flow occurs when the pressure across the seal exceeds the maximum sealing pressure of the seal, i.e., when $P>P_{max}$. Another assumption that may be made is that the pressure $P_1$ that is supplied by the flow generator is constant. Furthermore, it may be assumed that the volume $V_2$ between the first and second seals is constant.

Although certain assumptions, such as those discussed above, may be relied upon in modeling the behavior of the patient interface, the model may also take into account variations to those assumptions. For example, relative movements between the frame of the patient interface and the patient's face may be interpreted as variations of the maximum sealing pressure $P_{1max}$, $P_{2max}$ of the first and second seals $S_1$, $S_2$.

First Embodiment

Figure 3A:
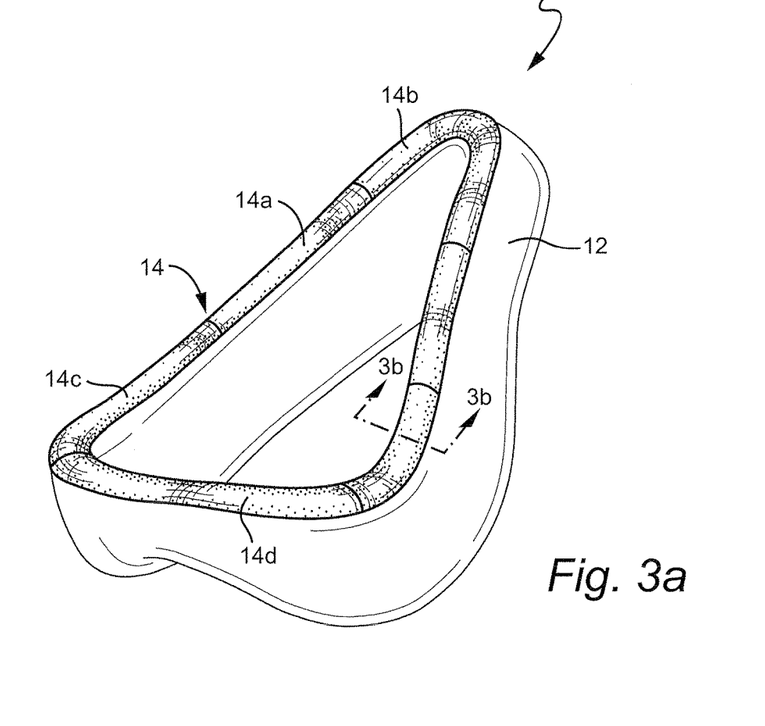
FIG. 3a illustrates a patient interface.
Figure 3B:
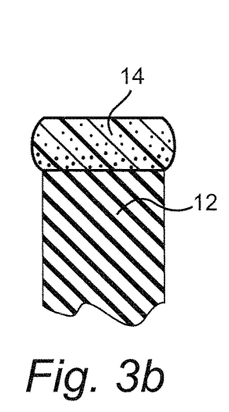
Figure 3C:
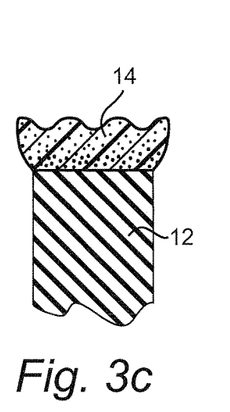
Figure 3D:
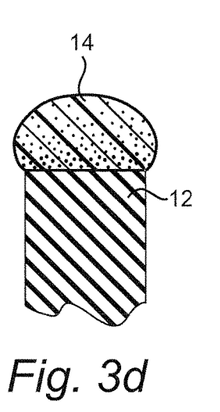
Figure 3E:
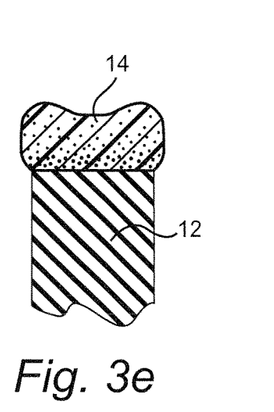

Referring to FIGS. 3a and 3b, a patient interface 10 according to one embodiment of the invention includes a cushion 12 having a filler layer 14 provided on the cushion 12. The filler layer 14 is adapted to be in contact with the patient's skin. The cushion 12 may be formed of, for example, silicone and the filler layer 14 may be formed of, for example, foam. The filler layer 14 may be, for example, adhesively attached to the cushion 12, for example by glue. The filler layer 14 may also be mechanically connected to the frame of the mask as a skin that envelops the cushion. In that case, the filler layer 14 may be replaced, for example in a manner similar to replacing the foam over earphones. The filler layer 14 may be connected at the same location as the cushion, on the cushion itself, or at another point on the frame. The filler layer 14 may also be silicone foam injected over the silicone cushion 12 so that the cushion and the filler layer are a single object. The filler layer 14 serves to fill gaps between the cushion 12 and the patient's skin. The filler layer 14 also reduces, or eliminates, vibrations of the cushion 12 and reduces any leak flow by increasing the resistance of the seal formed by the cushion 12. The filler layer 14 also diffuses any leak flow that may occur. Moreover, any leak flow passing through the filler layer 14 may inflate the filler layer 14 and permit the patient's skin to breathe. The filler layer 14 may be uniform in cross sectional shape and material, or the filler layer 14 may be made of differing materials in different areas 14a-14d and also differing shapes (as shown in FIG. 3b). The filler layer may be a closed loop or selected areas may be left empty.

Second Embodiment

Figure 4:
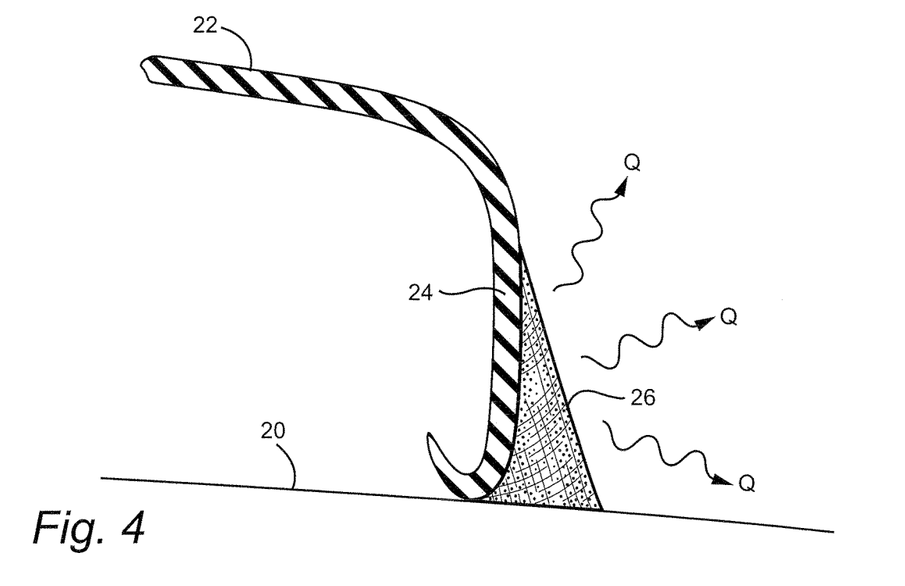
FIG. 4 illustrates a patient interface according to another embodiment of the present invention.

As shown in FIG. 4, an interface 22 may include a seal 24 in contact with the patient's skin 20. A diffuser 26 (e.g., of foam material) is provided outside the seal 24 of the interface 22 to increase the resistance to leak flow Q and diffuse any leak flow that may actually occur. The diffuser 26 may be connected to the seal 24 in a manner similar to the connection of the filler layer 14 to the cushion 12 of the first embodiment. However, unlike the first embodiment, in which only the filler layer 14 contact the patient's face, according to the second embodiment the seal 24 of the interface 22 and the diffuser 26 are provided in series and both contact the patient's face. Accordingly, in the second embodiment the "sealing" provided by the seal 24 and diffuser 26 is broader than the "sealing" provided by the first embodiment as the seal 24 and the diffuser increase the resistance to leak flow. It should be appreciated that the seal may provide very little, or no resistance, to leak flow while the diffuser 26 may be configured to limit the leak flow to small values. The diffuser 26 may be a porous material, for example a porous material that provides a high resistance to leak flow while providing compliance with the patient's face. The diffuser 26 may be mechanically connected to the interface 22 in a manner similar to the mechanical connection of the filler layer 14 to the cushion 12 discussed above with respect to the first embodiment. The diffuser 26 may also be silicone foam injected on the interface so that they are a single object. The diffuser 26 may also be attached to the interface 22 adhesively. Although the diffuser 26 is shown in FIG. 4 as being provided on the exterior of the interface 22, it should be appreciated that the diffuser may be provided in the interior of the interface 22 and diffuse any leak flow before it passes the seal 24. Such a configuration may also prevent explosive leakage from the interface 22.

Third Embodiment

Figure 5:
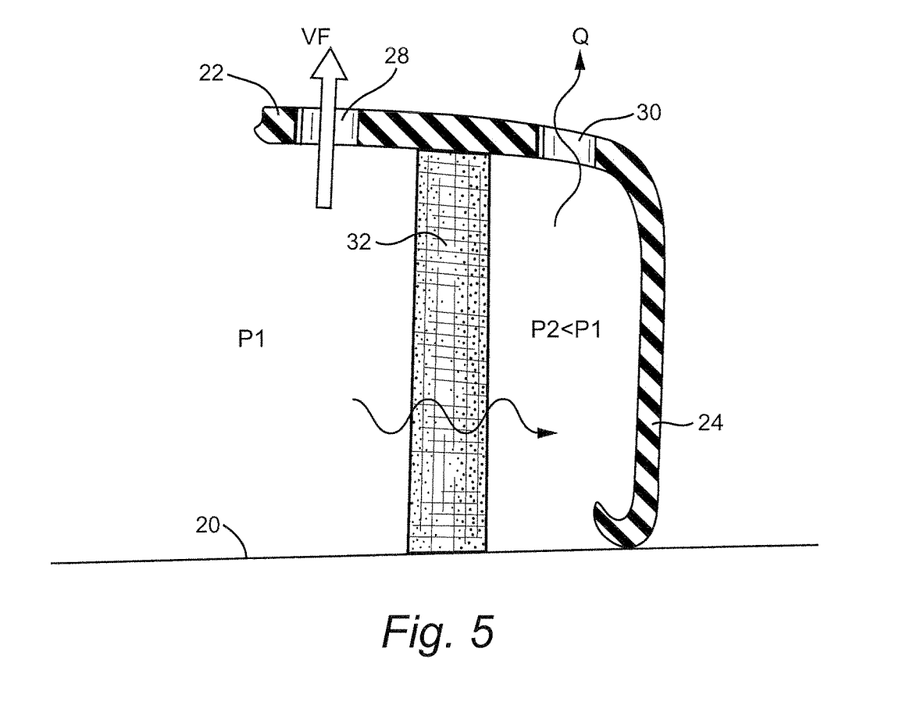
FIG. 5 illustrates a patient interface according to another embodiment of the invention.

Referring to FIG. 5, an interface 22 includes a primary seal 24 adapted to contact the patient's skin 20. The primary seal 24 may be, for example, silicone. A secondary seal 32 is placed inside the interface 22 and may also be in contact with the patient's face. The secondary seal 32 may be, for example, foam. The space between the primary seal 24 and a secondary seal 32 includes secondary vents 30 which are provided in addition to primary vents 28. A vent flow VF is vented through the primary vents 28. The volume between the primary seal 24 and the secondary seal 32 is vented through secondary vents 30 to create a local low-pressure area near the primary seal 24, i.e. P2<P1. Any leak flow across the secondary seal 32 will be vented through the secondary vents 30. The secondary vents 30 may be placed in an area of the patient interface where the vented leak flow Q will not disturb the patient.

Fourth Embodiment

Figure 6:
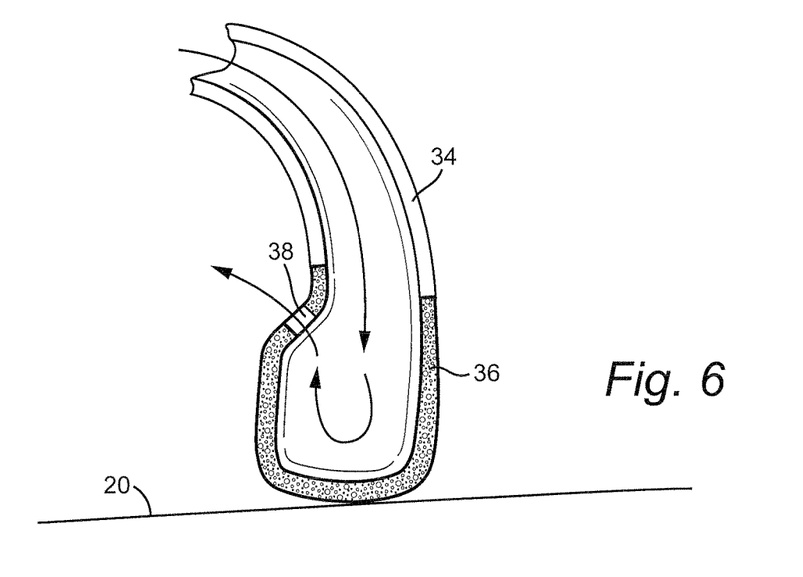
FIG. 6 illustrates a patient interface according to another embodiment of the invention.

Referring to FIG. 6, an air delivery hose or conduit 34 may be incorporated into a frame of the patient interface. The conduit 34 is connected to an inflatable cushion 36. The inflatable cushion 36 may comprise a hollow gel seal. The inflatable cushion 36 is pressurized against the patient's skin 20 by pressure force and the force caused by the deflection of the air flow through vents 38 formed in the inflatable cushion 36 that deliver the breathable gas to the patient. The flow generator of the breathing apparatus supplies breathable gas via the hose or conduit 34 to the patient interface. The hose or conduit 34 may be connected to the patient interface by an elbow, for example a swivel elbow. The flow generator delivers the flow to the elbow at a pressure $P_1$. Due to the resistance of the hose or conduit, and the elbow if provided, the pressure $P_1$ drops to a pressure $P_2$ which inflates the inflatable cushion 36. The drop in pressure is in the hose or conduit, and optional elbow, is $\Delta P_1 = P_1 - P_2$. The pressure of the flow of breathable gas is further reduced by the resistance of the vents 38, and the pressure drops to the therapy pressure $P_T$. The pressure drop from the vents is $\Delta P_2 = P_2 - P_T$. Therefore, in order for the correct therapy pressure $P_T$ to be delivered to the patient, the pressure $P_1$ supplied by the flow generator is $P_1 = P_T + \Delta P_2 + \Delta P_1$.

Fifth Embodiment

Figure 7A:
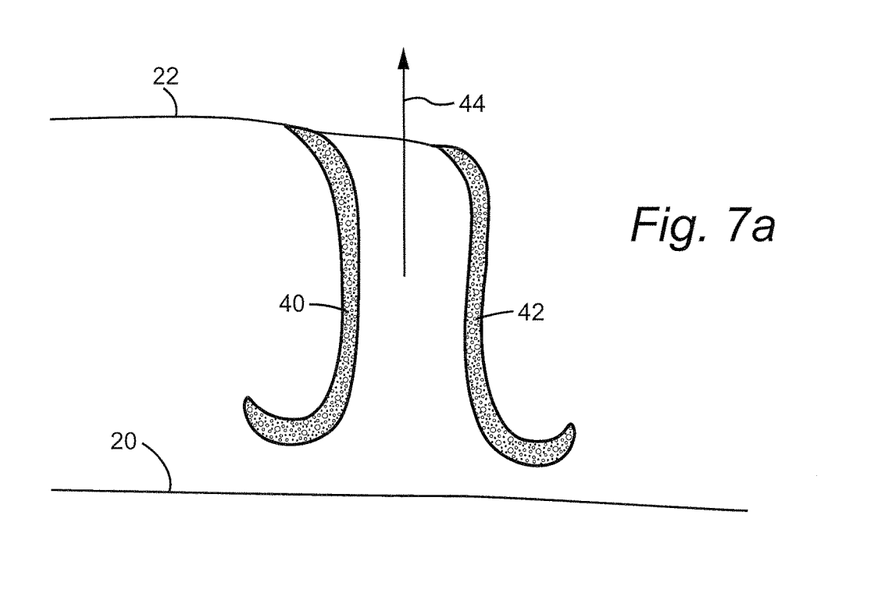
FIGS. 7a and 7b illustrate a patient interface according to another embodiment of the invention.
Figure 7B:
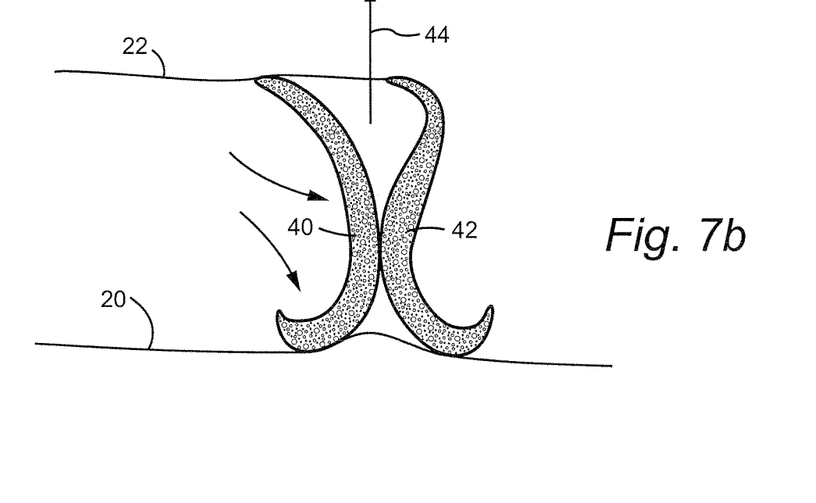

A patient interface according to another embodiment of the invention is shown in FIGS. 7a and 7b. The patient interface 22 includes first and second seals 40, 42 which form a seal against the patient's skin 20. A vacuum line 44 sucks any leak flow that may occur between the first and second seals 40 and 42 and deforms the seals 40 and 42, and the skin between them, into the position shown in FIG. 7b. The seals 40 and 42 may be formed, for example, as gel cushions. The vacuum may only be switched on, for example, when the second space is at a pressure higher than ambient.

Sixth Embodiment

Figure 8:
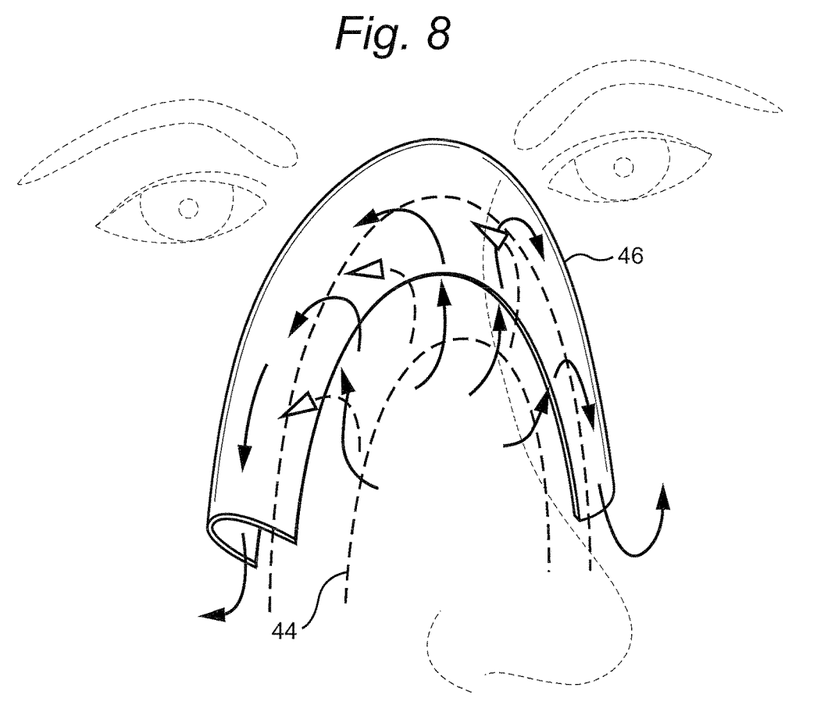
FIG. 8 illustrates a patient interface according to another embodiment of the invention.

According to another embodiment of the invention shown in FIG. 8, a leak cuff 46 may be provided over a seal 44 of a patient interface in the nasal bridge area of the patient's face. Any leak flow passing the seal 44 is directed by the leak cuff 46 around the nose bridge 45 of the patient and away from the patient's eyes 47 as shown by the arrows in FIG. 8, effectively redirecting the leak flow. It should be appreciated that the leak cuff 46 may be provided around the perimeter of the entire patient interface, or may be provided only in the nasal bridge region. It should also be appreciated that the leak cuff 46 may be configured to seal against the patient' face. It should further be appreciated that the leak cuff 46 may be provided to a dual wall cushion, in which case the leak cuff 46 may take the form of a third wall.

Seventh Embodiment

Figure 9:
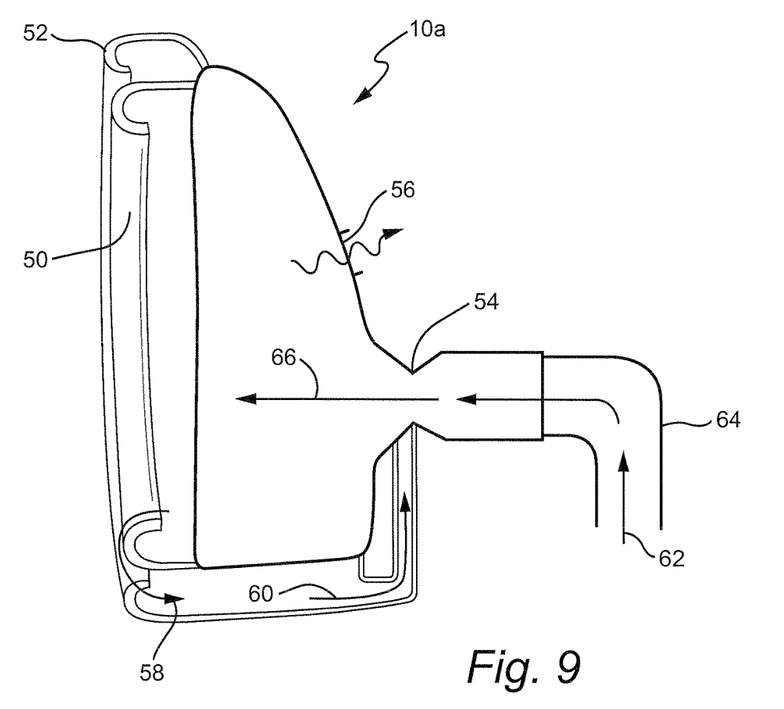
FIG. 9 illustrates a sectioned patient interface according to another embodiment of the invention.

A patient interface 10a according to another embodiment of the invention shown in FIG. 9 includes a first seal 50 and a second seal 52. The patient interface 10a also includes a convergent-divergent nozzle 54 in an elbow 64 attached to the patient interface 10a creating a Bernoulli effect. Any leak flow 58 that occurs between the first seal 50 and the second seal 52 is effectively re-circulated by the nozzle 54. The re-circulated leak flow 60 is added to the flow 62 delivered by the flow generator to provide a supply 66 of breathable gas to the patient.

The pressure between the first seal 50 and the second seal 52 should be lower than the pressure in the patient interface 10a, but slightly higher than the ambient pressure in order to avoid loss of the leak flow 58 to the ambient.

Eighth Embodiment

Figure 10:
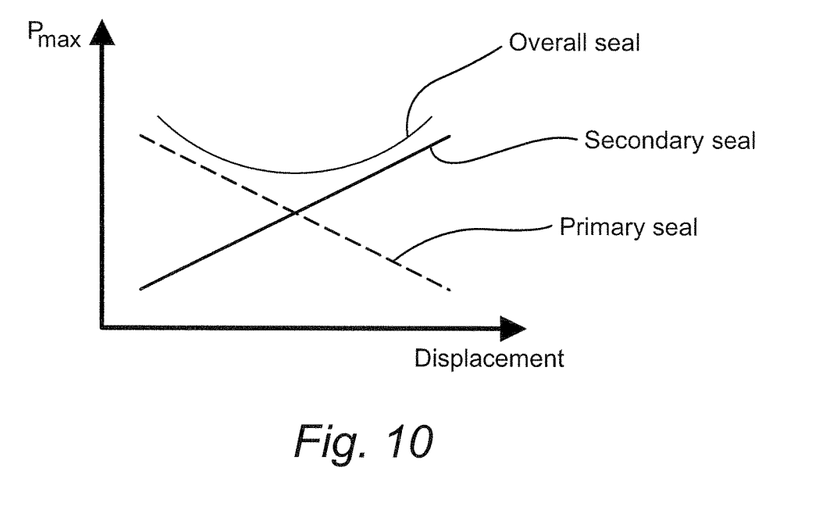
FIG. 10 is a diagram illustrating the operation of a patient interface having a primary seal and a secondary seal in accordance with another embodiment of the invention.

Referring to FIG. 10, a patient interface may include a primary seal and secondary seal. The primary seal has a higher maximum sealing pressure $P_{max}$ at a lower displacement of the patient interface with respect to the patient's face than the secondary seal. When the patient interface is displaced, the maximum sealing pressure of $P_{max}$ of the primary seal decreases while the maximum sealing pressure $P_{max}$ of the secondary seal increases. Such an arrangement may include a deformable patient interface frame, such as a mask frame, that automatically adjusts according to the load condition placed on the frame. After a certain amount of displacement, the secondary seal has a maximum sealing pressure $P_{max}$ that is higher than the maximum sealing pressure $P_{max}$ of the primary seal. As shown in FIG. 10, the maximum overall sealing pressure $P_{max}$ of the combination of the primary seal and the secondary seal is higher than either the maximum sealing pressure of the primary seal or the secondary seal alone.

Ninth Embodiment

Figure 11:
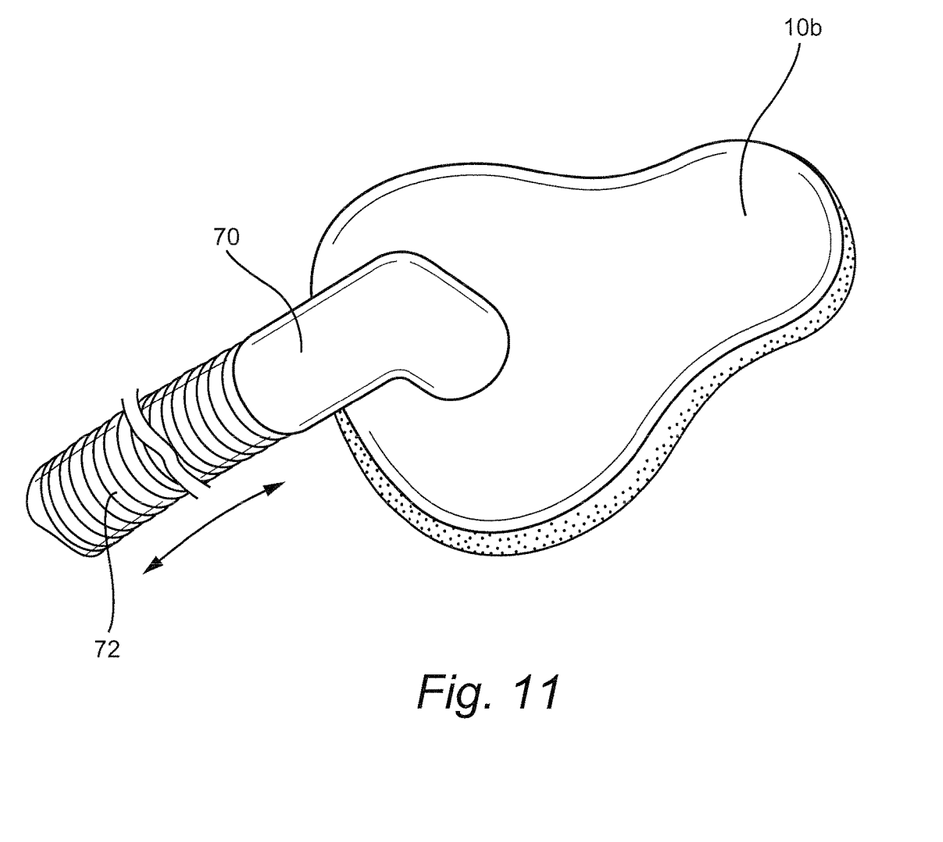
FIG. 11 illustrates a patient interface and an air delivery hose in accordance with another embodiment of the invention.

It is also possible to reduce the leak flow from the patient interface by considering other components of the breathing apparatus. As shown in FIG. 11, the patient interface 10b is connected to an air delivery conduit or hose 70. The conduit 70 includes a localized area 72 having a high axial deformability that can compensate for the pull of the conduit 70 on the patient interface 10b (i.e. tube drag). The conduit 70 may also be a retractable tube, for example as disclosed in U.S. Applications 60/973,902, filed Sep. 20, 2007, 60/987,825, filed Nov. 14, 2007, and 61/031,407, filed Feb. 26, 2008, the entire contents of all three being incorporated herein by reference.

It should be appreciated that the sample embodiments disclosed herein may be used in various NIPPV therapies, including Continuous Positive Airway Pressure (CPAP), Variable Positive Airway Pressure (VPAP), and Bi-level Positive Airway Pressure (BiPAP). In these therapies, a pressurized flow of breathable gas, e.g. air, may be supplied to a patient's airways at a pressure of, for example, between 4 cm $H_2O$ to 20 cm $H_2O$.

While the invention has been described in connection with what are presently considered to be the most practical embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. Furthermore, each individual component of any given assembly, one or more portions of an individual component of any given assembly, and various combinations of components from one or more embodiments may include one or more ornamental design features. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A patient interface for use in delivering a flow of breathable gas to an airway of a patient, the patient interface comprising:
   a flexible cushion adapted to contact the patient's face and seal a space between the patient interface and the patient's face at a positive pressure; and
   a means for reducing and diffusing leakage of gas from the space.

2. A patient interface according to claim 1, wherein the cushion is formed of a material non-permeable to the breathable gas.

3. A patient interface according to claim 1, wherein the cushion is formed of a material non-permeable to the breathable gas and a porous layer in parallel.

4. A patient interface according to claim 3, wherein the porous layer is adapted to contact the patient's face.

5. A CPAP apparatus comprising a patient interface according to claim 1.

6. A BiPAP apparatus comprising a patient interface according to claim 1.

7. A patient interface according to claim 1, wherein the cushion is formed of silicone.

8. A patient interface according to claim 1, wherein the means for reducing and diffusing leakage of gas from the space is configured to be inflated by the leakage of gas from the space.

9. A patient interface according to claim 1, wherein the means for reducing and diffusing leakage of gas from the space is adhesively attached to the cushion.

10. A patient interface according to claim 1, wherein when the patient interface is engaged with the patient's face, a distance between the cushion and the patient's face is less than a depth of the cushion.

11. A patient interface for use in delivering a flow of breathable gas to an airway of a patient, the patient interface comprising:

a flexible cushion adapted to contact the patient's face and seal a space between the patient interface and the patient's face at a positive pressure; and a leak reducing layer provided on the cushion and configured to reduce and diffuse leakage of gas from the space.

12. A patient interface according to claim 11, wherein the cushion is formed of a material non-permeable to the breathable gas.

13. A patient interface according to claim 11, wherein the leak reducing layer comprises a porous layer on the cushion and adapted to contact the patient's face.

14. A patient interface according to claim 13, wherein the porous layer is provided outside of the space.

15. A patient interface according to claim 14, wherein a maximum sealing pressure of the cushion decreases as the patient interface is displaced from the patient's face and a maximum sealing pressure of the porous layer increases as the patient interface is displaced from the patient's face.

16. A patient interface according to claim 11, wherein the leak reducing layer has a uniform cross sectional shape.

17. A patient interface according to claim 11, wherein the leak reducing layer forms a skin that envelopes the cushion.

18. A patient interface according to claim 17, wherein the leak reducing layer is removably attached to the cushion.

19. A patient interface according to claim 17, wherein the leak reducing layer is adapted to attach to a mask frame.

20. A patient interface according to claim 19, wherein the cushion is adapted to attach to the mask frame and the leak reducing layer is adapted to attach to the mask frame at the same location as the cushion.

21. A patient interface according to claim 19, wherein the cushion is adapted to attach to the mask frame and the leak reducing layer and the cushion are adapted to attach to the mask frame at different locations.

22. A patient interface according to claim 11, wherein the cushion and the leak reducing layer are formed from the same material.

23. A patient interface according to claim 11, wherein the leak reducing layer is formed of foam.

24. A patient interface according to claim 23, wherein the leak reducing layer is formed of silicone foam.

25. A patient interface according to claim 16, wherein the leak reducing layer is formed of different materials.

26. A patient interface according to claim 11, wherein the leak reducing layer has a non-uniform cross sectional shape.

27. A patient interface according to claim 26, wherein the leak reducing layer is formed of one material.

28. A patient interface according to claim 26, wherein the leak reducing layer is formed of different materials.

29. A patient interface according to claim 11, wherein the leak reducing layer envelopes the cushion.

30. A patient interface for use in delivering a flow of breathable gas to an airway of a patient, the patient interface comprising:
a flexible cushion adapted to contact the patient's face and seal a space between the patient interface and the patient's face at a positive pressure; and
means for diffusing gas from the space and increasing the resistance of the seal formed by the cushion.

31. A patient interface for use in delivering a flow of breathable gas to an airway of a patient, the patient interface comprising:
a flexible cushion adapted to contact the patient's face and seal a space between the patient interface and the patient's face at a positive pressure; and
a resistance layer provided on the cushion configured to diffuse gas from the space and increase the resistance of the seal to leakage of gas flow from the space.

32. A patient interface according to claim 31, wherein the resistance layer is formed of foam.

33. A patient interface according to claim 32, wherein the resistance layer is formed of silicone foam.

34. A patient interface according to claim 31, wherein the resistance layer is formed of different materials.

35. A patient interface according to claim 31, wherein the resistance layer is adhesively attached to the cushion.

36. A patient interface for use in delivering a flow of breathable gas to an airway of a patient, the patient interface comprising:
a flexible cushion adapted to contact the patient's face and seal a space between the patient interface and the patient's face at a positive pressure; and
means for diffusing leakage of gas from the space.

37. A patient interface for use in delivering a flow of breathable gas to an airway of a patient, the patient interface comprising:
a flexible cushion adapted to contact the patient's face and seal a space between the patient interface and the patient's face at a positive pressure; and
a diffusing layer provided on the cushion that diffuses leakage of gas from the space.

38. A patient interface according to claim 37, wherein the diffusing layer is formed of foam.

39. A patient interface according to claim 38, wherein the diffusing layer is formed of silicone foam.

40. A patient interface according to claim 37, wherein the diffusing layer is formed of different materials.

41. A patient interface according to claim 37, wherein the diffusing layer is adhesively attached to the cushion.

42. A patient interface according to claim 37, wherein the cushion is formed of silicone and the diffusing layer is formed of silicone foam.

* * * * *